United States Patent
Grawe et al.

(10) Patent No.: US 7,192,942 B2
(45) Date of Patent: *Mar. 20, 2007

(54) PROCESS FOR PRODUCTION OF CRYSTALS OF 11μ-BENZALDOXIM-ESTRA-4,9-DIENE DERIVATIVES, CRYSTALS OBTAINED THEREBY AND PHARMACEUTICAL PREPARATIONS CONTAINING THEM

(75) Inventors: Detlef Grawe, Kleinromstedt (DE); Hagen Gerecke, Jena (DE); Peter Hoesel, Jena (DE); Annette Eichardt, Buergel (DE); Sabine Gliesing, Jena (DE); Uwe Mueller, Jena (DE)

(73) Assignee: Schering AG, Berlin (DE)

( * ) Notice: Subject to any disclaimer, the term of this patent is extended or adjusted under 35 U.S.C. 154(b) by 358 days.

This patent is subject to a terminal disclaimer.

(21) Appl. No.: 10/417,559

(22) Filed: Apr. 17, 2003

(65) Prior Publication Data

US 2003/0225050 A1     Dec. 4, 2003

(30) Foreign Application Priority Data

Apr. 23, 2002  (DE) ................................ 102 18 109

(51) Int. Cl.
*A61K 31/56*    (2006.01)
*C07J 1/00*     (2006.01)
(52) U.S. Cl. ...................................... 514/179; 552/648
(58) Field of Classification Search ................ 552/648; 514/179
See application file for complete search history.

(56) References Cited

U.S. PATENT DOCUMENTS

| 5,534,270 | A | * | 7/1996 | De Castro ................... 424/490 |
| 5,693,628 | A | * | 12/1997 | Schubert et al. ............ 514/179 |
| 5,718,388 | A | | 2/1998 | Czekai et al. |
| 2004/0006241 | A1 | * | 1/2004 | Grawe et al. |

FOREIGN PATENT DOCUMENTS

| DE | 275 398 A1 | 1/1990 |
| DE | 694 19 151 T2 | 11/1999 |
| DE | 693 28 815 T2 | 2/2001 |
| DE | 695 23 781 T2 | 6/2002 |
| EP | 0 499 299 A2 | 8/1992 |
| EP | 0 648 778 A2 | 4/1995 |
| EP | 1157996 A1 * | 11/2001 |
| WO | 98/57648 | 12/1998 |

OTHER PUBLICATIONS

Norbert Rasenack et al: "Micronization of Anti . . . " Journal of Pharmaceutical Science, vol. 92, No. 1, Jan. 2003, pp. 35-44.

* cited by examiner

*Primary Examiner*—Barbara P. Badio
(74) *Attorney, Agent, or Firm*—Michael J. Striker

(57) ABSTRACT

The process for making crystals of a 11 β-benzaldoxim-estra-4,9-diene derivative having an average particle size of from 3 μm to 25 μm and a maximum particle size of 100 μm, includes subjecting a supersaturated solution containing a special 11β-benzaldoxim-estra-4,9-diene derivative of formula (I) to a wet milling by a wet milling apparatus while crystallizing, In order to obtain a primary particle suspension. Crystals obtained according to this process and pharmaceutical preparations containing them are also described and are part of the invention.

23 Claims, 4 Drawing Sheets

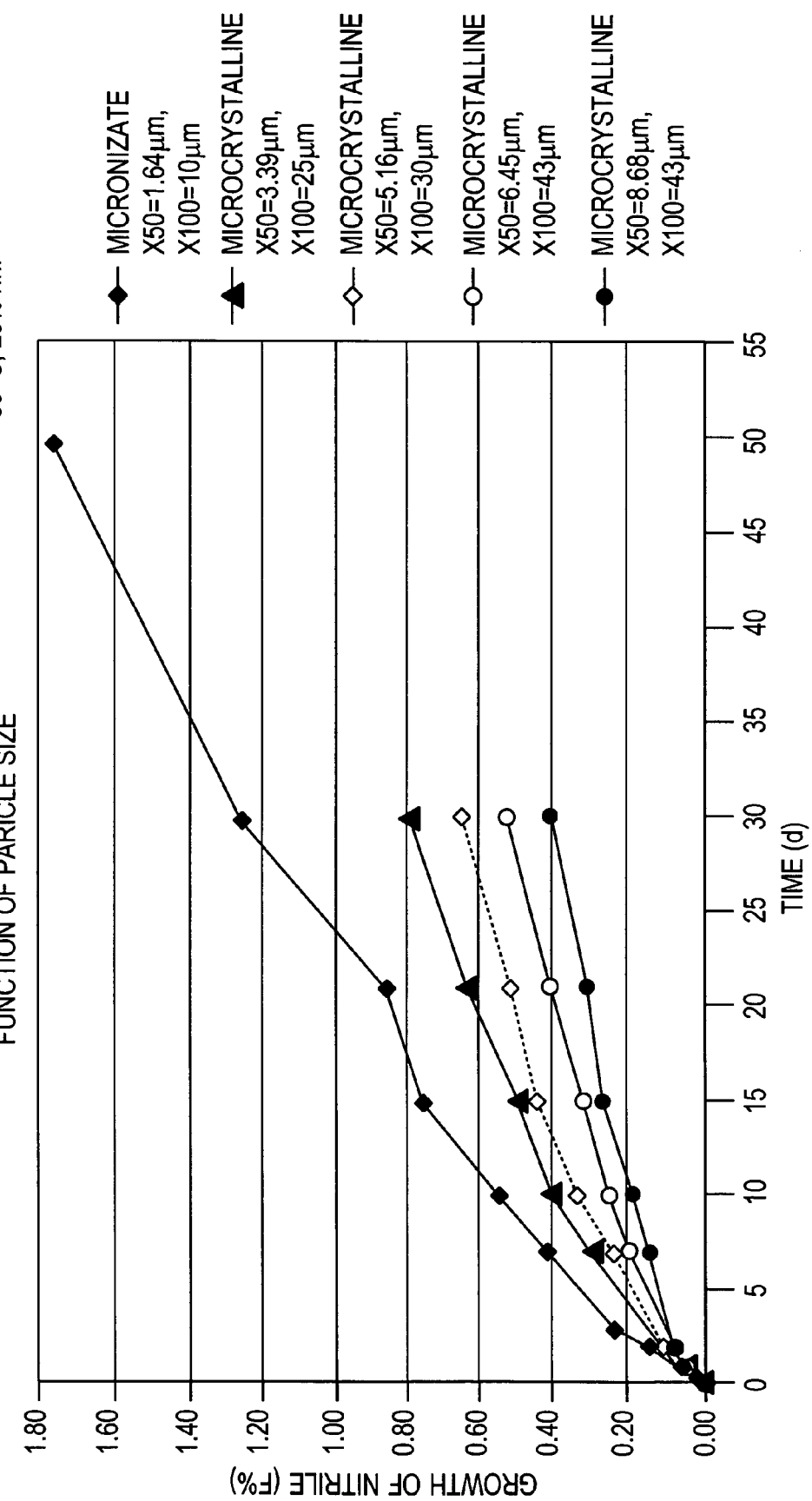

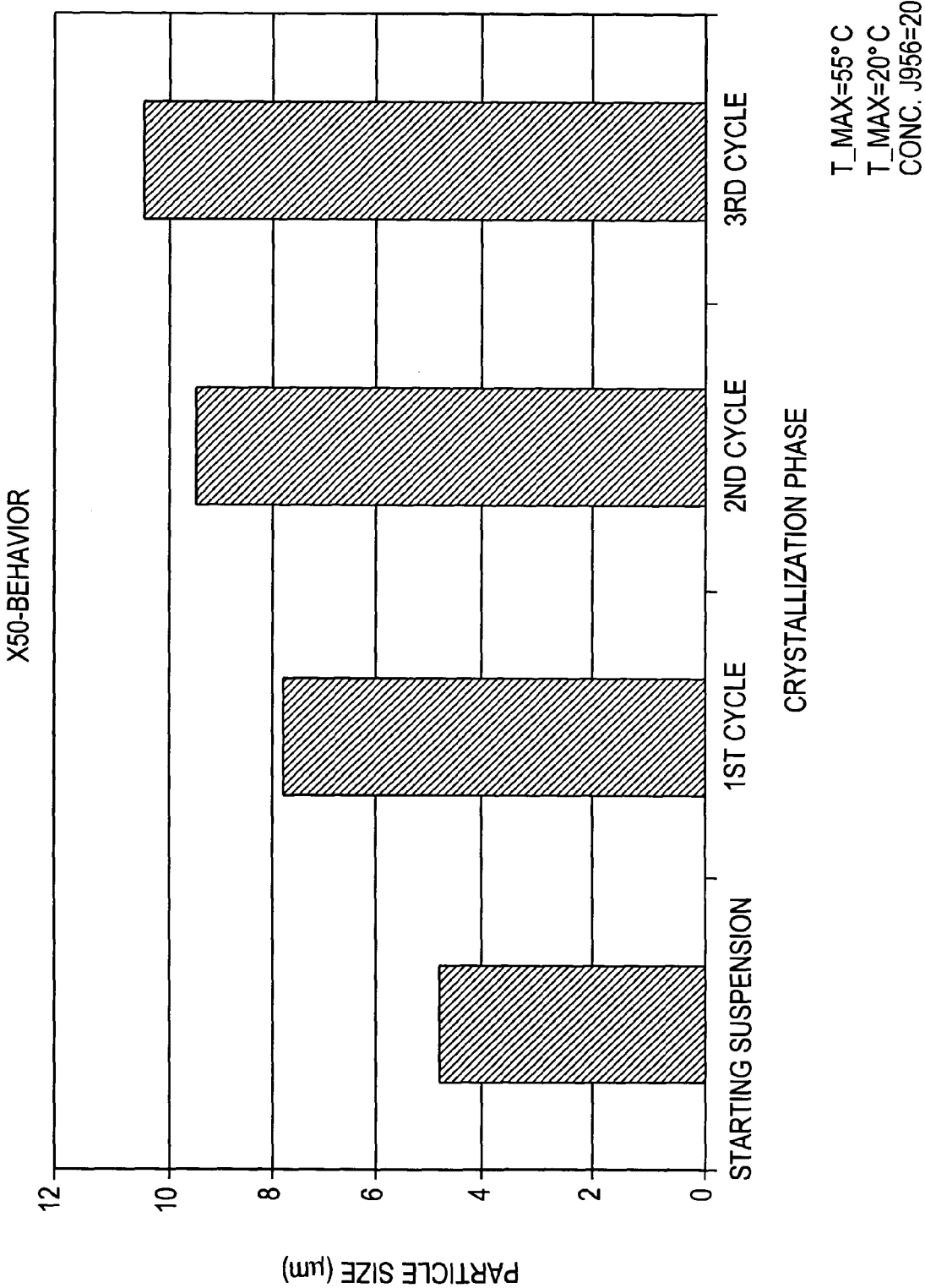

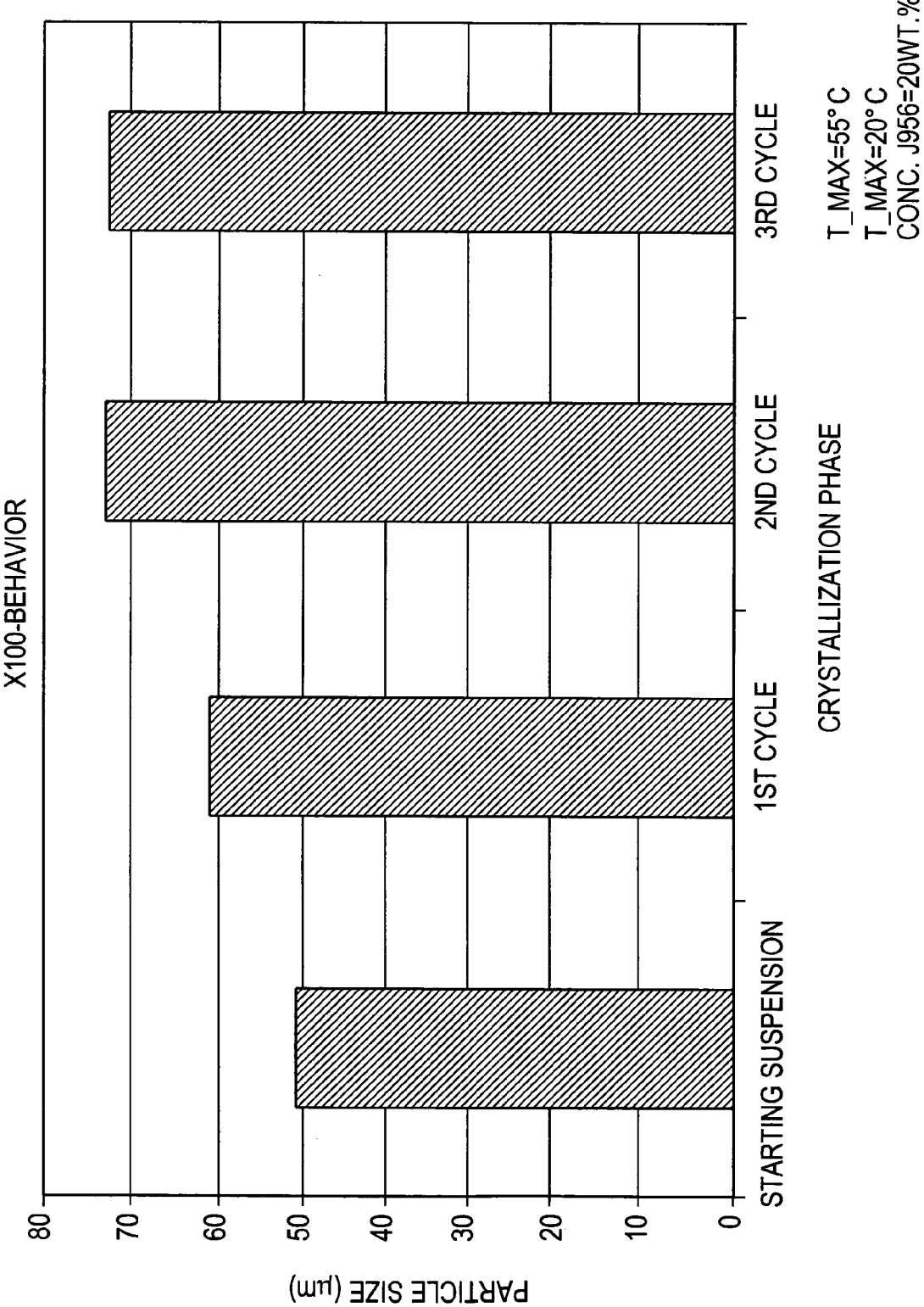

PROCESS FOR PRODUCTION OF CRYSTALS OF 11µ-BENZALDOXIM-ESTRA-4,9-DIENE DERIVATIVES, CRYSTALS OBTAINED THEREBY AND PHARMACEUTICAL PREPARATIONS CONTAINING THEM

BACKGROUND OF THE INVENTION

1. Field of the Invention

The invention relates to a process for production of crystals of 11β-benzaldoxim-estra-4,9-diene derivatives, whose average particle size is in a predetermined range and whose maximum particle size does not exceed a predetermined value, to the crystals obtained thereby and to the pharmaceutical preparations containing them, especially to low-dosage preparations.

2. Description of the Related Art

EP 0 648 778 A2 discloses 11β-benzaldoxim-estra-4,9-diene derivatives. The synthesis and purification of these compounds is described in that reference. However the crystallization and shaping step is not descried in that reference. Like most steroids these compounds are crystallized from a suitable solvent. Among other things, the particle size distribution or particles sizes that arise during conventional cooling and crystallization are not disclosed.

For low dosage preparations, which contain the effective ingredient in only comparatively small amounts, for example 0.1 to 2 percent by weight, special requirements are put on the homogeneity of the active ingredient distribution (uniform content, CUT) and dissolution kinetics. In these low dosage preparations the active ingredient present in very limited amounts is diluted with the other medicinal ingredients to a considerable extent. A certain average particle size should not be exceeded and the scatter or spread of the distribution should not be too great, so that the uniformity of the effective ingredient distribution remains nearly constant. This maximum particle size depends on the dosage and the application form and can be determined statistically. Furthermore with low dosage formulations the fact that smaller particles dissolve more rapidly in the stomach than larger particles must be considered. A certain particle size must not be exceeded in order to meet the requirement in regard to dissolution kinetics.

Currently crystallizates are micronized in a jet mill according to traditional engineering to obtain the required uniformity of effective-ingredient distribution and dissolution kinetics, especially for low-dosage preparations. Average grain sizes of from 1.5 to 3 µm are obtained. An enormous increase in surface area as well as a thermodynamic activation of the surface occurs by partial amorphization and/or by considerable destruction or perturbation of lattice structure. These physical changes cause a considerable chemical destabilization of the effective ingredient not only in its pure form, but also and above all, when it is present in a pharmaceutical preparation.

The carbamate functional group of the above-mentioned 11β-benz-aldoxim-estra-4,9-diene derivative decomposes to form a nitrile by splitting off ethylamine and $CO_2$. The use of a micronizate thus leads to medicinal preparations, in which the effective ingredient is not sufficiently stable under ICH, i.e. (40° C., 70% relative humidity).

Lowering the milling pressure of course leads to a slight increase in the average particle size, but also to an undesirable increase in its spread. However a certain minimum pressure is absolutely required for operation of the mill. It has currently been possible to use the form of the solid to obtain better chemical stability through the micronization parameters to an only very limited extent.

SUMMARY OF THE INVENTION

It is an object of the present invention to provide a process for making crystals of 11β-benzaldoxim-estra-4,9-diene derivatives, which do not have the disadvantages of the known prior art processes and which fulfill the requirements of low-dosage preparations.

According to the invention this object is attained by a process for making crystals of a 11β-benzaldoxim-estra-4,9-diene derivative, whose average grain or particle size is in a predetermined range and whose maximum particle size does not exceeded a predetermined value. This process comprises subjecting a supersaturated solution containing the 11β-benzaldoxim-estra-4,9-diene derivative to a wet milling by means of a wetting milling apparatus while crystallizing, in order to obtain a primary particle suspension;

wherein said 11β-benzaldoxim-estra-4,9-diene derivative is a compound of formula (I), or a pharmacologically acceptable salt thereof:

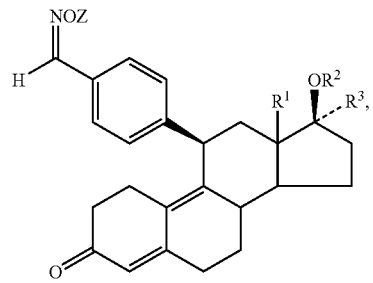

(I)

wherein $R^1$ represents hydrogen or an alkyl group with 1 to 6 carbon atoms;

$R^2$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or a —$CONHR^4$ group, $R^3$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, or a —$(CH_2)_n$—$CH_2X$, an —$OR^5$ group, a —$(CH_2)_o$—CH=CH$(CH_2)_p$—$R^6$ group or —$(CH_2)_q$C=$CR^7$;

wherein n is 0, 1 or 2, o is 0, 1, 2 or 3, p is 0, 1 or 2 and q is 0, 1 or 2;

wherein X represents hydrogen, a fluoro group, a chloro group, a bromo group, an iodo group, a cyano group, an azido group, a rhodano group, an —$OR^5$ group or an —$SR^5$ group;

wherein Z represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms, a —$CONHR^4$ group, a —$COOR^4$ group, an alkali metal atom or an alkaline earth metal atom;

wherein $R^4$ represents an alkyl group with 1 to 10 carbon atoms, an aryl group with 1 to 10 carbon atoms, an aralkyl group with 1 to 10 carbon atoms or an alkylaryl group with 1 to 10 carbon atoms;

wherein $R^5$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms;

wherein $R^6$ represents a hydrogen, a hydroxy group, an alkyl group with 1 to 10 carbon atoms, an alkoxy group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or an acyloxy group with 1 to 10 carbon atoms; and wherein $R^7$ represents a hydrogen, a fluoro group, a chloro group, a bromo group, an iodo group, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms.

With the process according to the present invention it is surprisingly possible to obtain steroid crystals which are sufficiently stable and which are adjusted in regard to their particle size parameter and thus correct in regard to pharmaceutical requirements for homogeneity of the active ingredient distribution (CUT) and dissolution kinetics for low-dosage formulations. Furthermore the grain size distribution for a certain dosage can be made with a high accuracy and reproducibility. Furthermore the process according to the invention can be performed simply, rapidly and in a cost-effective manner. The steroid crystals can preferably be isolated without impairing their grain size distribution and dried.

The compound of formula (I) used in the process is 11β-{4-[(ethylamino-carbonyl)oximinomethyl]phenyl}-17β-methoxy-17α-methoxymethyl-estra-4,9-dien-3-one (subsequently designated as J956) in a preferred embodiment of the process according to the invention. The use of this particular compound of formula (I) in the process according to the invention provides the above-described advantages in a particularly good manner.

BRIEF DESCRIPTION OF THE DRAWING

The objects, features and advantages of the invention will now be illustrated in more detail with the aid of the following description of the preferred embodiments, with reference to the accompanying figures in which:

FIG. 2 is a graphical illustration showing the course of nitrile formation in J956 for various particles size samples of J956;

FIG. 3 is a graphical illustration of the behavior of the particle size of the crystalline particles during the course of the crystallization process according to the invention; and FIG. 4 is another graphical illustration of the behavior of the particle size during the course of the crystallization process according to the invention

DESCRIPTION OF THE PREFERRED EMBODIMENTS

Figure 1:
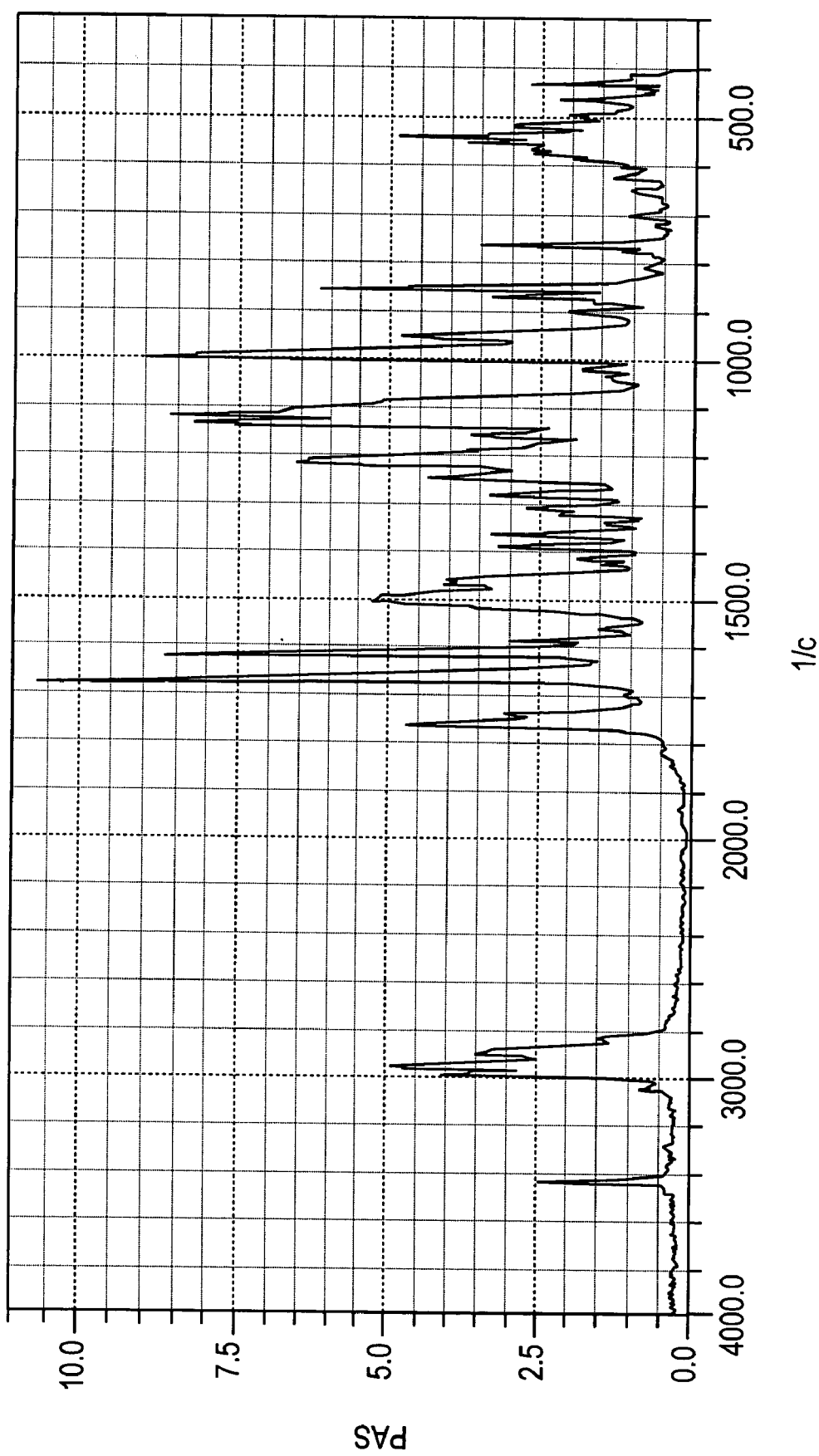
FIG. 1 is the IR spectrum of 11β-{4-[(ethylaminocarbonyl)oximino-methyl]phenyl}-17β-methoxy-17α-methoxymethyl-estra-4,9-dien-3-one (J956)

The average particle size preferably amounts to from 3 μm to 25 μm, especially from 7 μm to 15 μm. The maximum particle size preferably does not exceed 100 μm, more preferably 80 μm. The "maximum particle size" means that no particle has a size that is greater than the stated value.

Within these limits for the average particle size and the maximum particle size the particle size distribution is selected in a beneficial way so that the pharmaceutical specifications regarding CUT and dissolution kinetics correspond to those for low-dose formulations.

In the process according to the invention a supersaturated solution of the steroid is used. The solution contains the steroid as a solute, which is dissolved for that purpose in a solvent. The term "solvent" is understood to also encompass mixtures of different solvents. A supersaturated solution used in the process according to the invention contains more dissolved material than it would when the solution is in thermodynamic equilibrium. Supersaturated solutions, in which crystal nuclei spontaneously form, can be used in the process according to the invention.

In a preferred embodiment of the process according to the invention the supersaturated solution contains from 10 percent by weight to 30 percent by weight, preferably about 20 percent by weight, of the steroid compound of formula (I), in relation to the supersaturated solution. The above-described advantages of the process according to the invention can be achieved in an especially beneficial manner with these supersaturated solutions.

In preferred embodiments of the process the solvent used to prepare the supersaturated solution is ethyl acetate, which has proven to be particularly good for making supersaturated solutions of the compounds of formula (I).

The preparations of the supersaturated solutions can occur in the usual manner. Preferably the supersaturated solution is made by dissolving the steroid in a solvent at a temperature below the boiling point and subsequently cooling to a temperature above the freezing point of the solution. If the ethyl acetate is used as the solvent for the supersaturated solution in the process according to the invention, the heating can occur, for example, at about 70° C., until the compound of formula (I) has dissolved in the ethyl acetate and the resulting solution appears to be clear. Cooling can take place during a period from 10 minutes to one hour, preferably 15 minutes to 30 minutes, at about 50 to 10° C., preferably 35 to 30° C. One skilled in the art can ascertain the parameters for making a supersaturated solution with another solvent than ethyl acetate and with another steroid other than J956 by simple tests without more.

The crystallization is advantageously performed in a vessel, which is equipped with a stirrer. For example, the crystallization vessel can be equipped for that purpose.

In the process according to the invention wet milling is performed by a wet milling apparatus during crystallization. The crystallization can proceed from the saturated solution, since the wet milling has been started. Suitable apparatus for wet milling are dispersion tools and homogenizers, such as rotor-stator apparatuses, stirring mills, roller mills and colloid mills.

The manufacture of the crystals according to the invention occurs, as already described above, by crystallization from a solvent or solvent mixture, preferably by cooling a supersaturated ethyl acetate solution. During the crystallization a wet milling is performed by means of a wet milling apparatus, especially a rotor-stator apparatus or a colloid mill. The wet milling is performed either shortly after crystallization has begun or before it has begun. The apparatus for wet milling can be used immediately as an additional stirring device in the crystallization vessel or in a by-pass loop that goes around the crystallization vessel. The use of the by-pass loop is especially beneficial, since the apparatus is used at the same time as a supply unit. If a rotor-stator apparatus is used, the peripheral rotation speed can be 10 m/s to 50 m/s, preferably 20 m/s to 40 m/s. A very high secondary nuclei formation rate is produced by the additional energy input caused by the wet milling, especially by the rotor-stator apparatus. The individual crystal growth is greatly reduced because of that energy input. Also the inevitably formed agglomerates are broken up in narrow gaps. Thus a fine primary particle size is the result, whose average particle size is between 3 μm and 5 μm and whose maximum particle size is not greater than 25 μm to 60 μm. These particle parameters can already be sufficient for low dose formulations.

In order to be able to make crystals that meet the pharmaceutical requirements, even for larger particle sizes, with a definite particle size distribution with suitable accuracy and better reproducibility, the primary suspension is preferably subjected to an oscillatory temperature profile. For that purpose the fine primary suspension produced is heated to a temperature $T_{max}$ below the solubility limit of the primary particles in the suspension and subsequently cooled slowly to a temperature $T_{min}$, which is above the freezing point of the suspension. On heating the fine-grained fraction of the primary particle suspension is dissolved and precipitated on the particle size fraction present during the cooling process. Because of that a definite shift in the particle size distribution to the larger range occurs. Preferably $T_{max}$ is selected so that between 10 and 90, preferably 20 to 50 and more preferably about 30, percent by weight of the primary particles are dissolved during the heating. The fraction of dissolved primary particles is selected according to the predetermined grain size, which again is determined by the type of low-dosage formulation. If a higher proportion of the primary particles dissolve, larger-sized or coarser particles result.

In a preferred embodiment of the process according to the invention $T_{min}$ is selected so that the dissolved primary particles substantially re-crystallize again. If it is particularly desirable to reduce the losses of the compound of formula (I), nearly all of the dissolved primary particles are re-crystallized on the still remaining primary particles.

It is especially preferable when the cooling from $T_{max}$ to $T_{min}$ occurs during 1 minute to 10 hours, especially during 0.5 hours to 2 hours.

The cooling side of the temperature profile should be controlled so that the fresh nuclei formation is kept as small as possible. The size of this coarsening depends on the amount of the crystallizate dissolved in the heating cycle, which again is determined by the position of both temperatures $T_{max}$ and $T_{min}$ in relation to the solubility limit and the solid concentration of the suspension. This heating-cooling cycle can be repeated often, preferably 1 to 10 times, until the desired particle size distribution is obtained. The controlling parameters are thus $T_{max}$, $T_{min}$ and the number of cycles. The more the desired coarsening, the less $T_{max}$ should be. Thus one can approach the desired final particle size with small steps. The development of the dissolved portion of the crystallizate in the heating periods is thus dimensioned so that the maximum particle diameter increases still only to a very small extent and the coarsening occurs in the region of the fine particles. Thus, for example, during dissolution and re-crystallization of 40 percent of the J956 precipitated from a 20 percent by weight ethyl acetate solution, the average particle diameter (×50) increases from 4.9 μm to 7.8 μm while the increase of the maximum particle size (×100) is scarcely measurable. That means that the particle size distribution is considerably narrowed during growth of the average value (×50) of the particle diameter. This effect is especially advantageous for pharmaceutical applications, especially for obtaining suitable CUT values and dissolution properties.

After passing through the oscillatory temperature profile the obtained crystal suspension can be filtered and washed with a solvent, since the steroid is only soluble to a small extent, for example less than 1 percent by weight. For example, these solvents are methyl-t.-butyl ether, hexane, heptane, water or mixtures of two or more of these solvents. Because of that in subsequent drying processes, which occur preferably by a drying gas or in vacuum directly in the filtration unit, bridge formation and agglomeration of the particles are avoided.

The drying can occur by convection or vacuum drying in a stirred or moving bed.

When a conventional filtration and drying is difficult and leads to impairment of the particle size distribution produced during the crystallization, for example in the case of very fine particle sizes, alternatively the filtered and is washed filter cake is suspended with a suspending liquid. The suspending liquid should be a liquid, preferably water, in which the steroid is only slightly soluble, for example less than one percent by weight. The obtained suspension can be converted into the dried solid form of the steroid by spray drying.

The subject matter of the invention also includes crystals of the compound of formula (I), which are obtained by the above-described process according to the invention. Reference is made to the description of the process for obtaining the crystals described herein.

If the steroid 11β-{4-[(ethylamino-carbonyl)oximinomethyl]phenyl}-17β-methoxy-17α-methoxymethyl-estra-4,9-dien-3-one is used as the compound of formula (I), the X-ray powder diffraction data shown in Table I below and the IR spectrum shown in FIG. 1 are obtained for this steroid.

TABLE I

COMPARISON OF THEORETICAL AND EXPERIMENTAL d and l VALUES FOR J956 FROM X-RAY POWDER DIFFRACTION DATA

| $d_{obs}$(Å) | $l_{obs}$ | $d_{obs}$(Å) | $l_{obs}$ | h k l |
|---|---|---|---|---|
| N/A | — | 12.992 | 10.3 | 2 0 0 |
| 10.34 | 32.7 | 10.322 | 97.2 | 0 0 1 |
| 9.56 | 18.7 | 9.560 | 51.1 | 1 1 0 |
| 9.30 | 0.9 | 9.302 | 4.7 | -2 0 1 |
| 7.25 | 4.3 | 7.243 | 13.6 | 2 0 1 |
| 6.63 | 14.5 | 6.624 | 42.3 | 3 1 0 |
| 6.26 | 9.6 | 6.253 | 31.8 | -4 0 1 |
| 6.14 | 26.4 | 6.137 | 54.3 | -3 1 1 |
| 5.27 | 14.5 | 5.273 | 33.1 | -2 0 2 |
| 5.14** | 100.0 | 5.143 | 50.3 | 3 1 1 |
|  |  | 5.140 | 100.0 | 0 2 0 |
| 4.78 | 10.9 | 4.780 | 21.7 | 2 2 0 |
| 4.73 | 7.3 | 4.728 | 12.5 | -1 1 2 |
| 4.64** | 43.1 | 4.638 | 47.3 | 5 1 0 |
|  |  | 4.637 | 53.1 | -5 1 1 |
| 4.60 | 15.7 | 4.601 | 28.3 | 0 2 1 |
| 4.50 | 10.1 | 4.499 | 14.3 | -2 2 1 |
| 4.43 | 4.6 | 4.429 | 11.2 | 2 0 2 |
| 4.19 | 18.9 | 4.192 | 36.1 | 2 2 1 |
| 4.03 | 8.2 | 4.031 | 15.5 | 4 2 0 |
| 3.97 | 3.5 | 3.971 | 5.8 | -4 2 1 |
| 3.92 | 6.0 | 3.915 | 12.8 | 5 1 1 |
| 3.74 | 4.3 | 3.737 | 9.6 | 3 1 2 |
| 3.63 | 2.8 | 3.622 | 6.5 | 4 0 2 |
| 3.57 | 4.8 | 3.574 | 8.7 | -7 1 1 |
| 3.45 | 4.0 | 3.449 | 7.1 | -4 2 2 |
| 3.40 | 11.5 | 3.398 | 15.0 | 1 3 0 |
| 3.35 | 10.8 | 3.358 | 12.8 | 2 2 2 |
| 3.26 | 6.6 | 3.259 | 5.8 | -1 3 1 |

TABLE I-continued

COMPARISON OF THEORETICAL AND EXPERIMENTAL d and l
VALUES FOR J956 FROM X-RAY POWDER DIFFRACTION DATA

| $d_{obs}(Å)$ | $l_{obs}$ | $d_{obs}(Å)$ | $l_{obs}$ | h k l |
|---|---|---|---|---|
| 3.19 | 4.3 | 3.196 | 5.2 | 1 3 1 |
| 2.97 | 7.1 | 2.968 | 8.7 | 3 3 1 |

Two crystal forms of the compound J956 are known, but only one of these forms is pharmaceutically relevant. The above-described process according to the invention produces this pharmaceutically relevant crystal form and the X-ray powder diffraction data are given in Table I above. Comparison of the observed d-values with the theoretical d-values shows that the deviation is in the range of less than 1%.

The subject matter of the invention also includes pharmaceutical formulations or preparations, which contain the crystals of the medicinally effective ingredient obtained according to the process of the invention. As pharmaceutically effective medicinally effective ingredient, for example hard gelatin capsules or tablets with and without coatings are used for peroral administration. The drugs or medicines made with the medicinally effective ingredient should not impair the chemical and crystalline stability of the microcrystals. This can be achieved by including a light protective means or agent with the medicinally effective ingredient, for example a colored capsule jacket or applying a colored coating;

not including a surface-increasing adjuvant, such as a highly dispersed silicon dioxide;

using no or only water as solvent or auxiliary agent, and/or keeping the moisture content of the medicinally effective ingredient low by a sufficient drying.

An example of a suitable capsule recipe or formula is provided in Table II.

TABLE II

SUITABLE CAPSULE RECIPE FOR
COMPOSITION CONTAINING 1 MG OF J956

| SUBSTANCE | AMOUNT |
|---|---|
| J956, microcrystalline | 1.000 mg |
| Microcrystalline cellulose | 102.480 mg |
| Magnesium stearate | 0.520 mg |
| Hard gelatin capsule, size 3 | 1 piece |
| Capsule filling mass | 104.000 mg |

In table III an example of a suitable tablet recipe is provided.

TABLE II

SUITABLE TABLET RECIPE FOR
COMPOSITION CONTAINING 1 MG OF J956

CORE:

| J956, microcrystalline | 1.00 mg |
|---|---|
| Lactose monohydrate | 33.8 mg |
| Corn starch | 18.0 mg |
| Maltodextrin (10% water) | 6.0 mg |
| Na carboxymethyl starch | 0.6 mg |
| Glycerol monobehenate | 0.6 mg |

SHELL:

| Hydroxypropylmethyl cellulose | 1.125 mg |
|---|---|
| Talcum | 0.225 mg |
| Titanium dioxide | 0.625 mg |
| Iron oxide, yellow pigment | 0.020 mg |
| Iron oxide, red pigment | 0.005 mg |

An essential result of the invention is that microcrystals of the steroid of formula (I) are obtained, which are chemically considerably more stable than currently known micronizates, since first they have a reduced specific surface area and second they have crystalline surfaces that are unperturbed and highly crystalline.

In FIG. 2 the stability of the microcrystals regarding nitrile formation under thermal stress (80°, 28% relative humidity) is shown in comparison to the micronizate. It shows that the microcrystals with increased particle size in comparison to a micronizate have a considerably improved stability, which results in a reduced generation of nitrile.

Another result is that the microcrystals of the steroid of formula (I) obtained by the process according to the invention correspond in regarding to their particle size distribution and solubility properties to the pharmaceutical requirements of drugs regarding CUT and dissolution properties.

It has been shown that the obtained release values and grain size distribution uniformity (CUT) of the microcrystals of the invention are not inferior to those using micronized solids of the prior art for comparison (Table IV to Table VII) for the 1 mg capsule and 1 mg tablet examples. The release values were compared in a test medium, which comprises 0.3% SDS in water, with paddle stirrIng, 100 rpm.

TABLE IV

J956: COMPARATIVE RELEASE VALUES IN % FOR
COMPARISON OF 1 mg CAPSULE WITH A MICRONIZED
EFFECTIVE INGREDIENT TO 1 mg CAPSULE WITH
MICROCRYSTALLINE SOLIDS

| PARTICLE DIAMETER (μm) | | RELEASE in % | | | | |
|---|---|---|---|---|---|---|
| X50 | X100 | 0 min | 10 min | 20 min | 30 min | 45 min |
| 3.4 | 25 | 0 | 90.7 | 97.3 | 98.1 | 99.9 |
| 5.2 | 30 | 0 | 89.8 | 93.5 | 93.4 | 95.6 |
| 6.6 | 43 | 0 | 93.2 | 95.9 | 96.7 | 96.8 |
| 8.7 | 43 | 0 | 93.5 | 96.7 | 98.5 | 99.7 |
| 14.1 | 87 | 0 | 90.2 | 95.3 | 96.0 | 96.3 |
| Micronizate | | 0 | 92.1 | 94.3 | 94.6 | 94.9 |

TABLE V

J956: CUT VALUE SPREAD FOR 1 mg CAPSULE WITH A
MICRONIZED EFFECTIVE INGREDIENT VERSUS 1 mg
CAPSULE WITH MICROCRYSTALLINE SOLIDS

| PARTICLE DIAMETER (μm) | | Confidence | |
|---|---|---|---|
| X50 | X100 | Interval % | RSD, % |
| 3.4 | 25 | 2.23 | 3.56 |
| 5.2 | 30 | 1.20 | 2.08 |

TABLE V-continued

J956: CUT VALUE SPREAD FOR 1 mg CAPSULE WITH A MICRONIZED EFFECTIVE INGREDIENT VERSUS 1 mg CAPSULE WITH MICROCRYSTALLINE SOLIDS

| PARTICLE DIAMETER (µm) | | Confidence | |
|---|---|---|---|
| X50 | X100 | Interval % | RSD, % |
| 6.6 | 43 | 1.08 | 1.57 |
| 8.7 | 43 | 0.93 | 1.38 |
| 14.1 | 87 | 1.77 | 2.50 |
| Micronizate | | 1.72 | 2.56 |

TABLE VI

J956: COMPARATIVE RELEASE VALUES IN % FOR COMPARISON OF 1 mg TABLET WITH A MICRONIZED EFFECTIVE INGREDIENT TO 1 mg TABLET WITH MICROCRYSTALLINE SOLIDS
Test Medium: 0.3% SDS in water, paddle, 100 rpm

| PARTICLE DIAMETER (µm) | | RELEASE in % | | | | |
|---|---|---|---|---|---|---|
| X50 | X100 | 0 min | 10 min | 20 min | 30 min | 45 min |
| 10.6 | 73 | 0 | 73.7 | 90.3 | 91.85 | 96.6 |
| Micronizate | | 0 | 92.1 | 94.3 | 94.6 | 94.9 |

TABLE VII

J956: CUT VALUE SPREAD FOR 1 mg TABLET WITH A MICRONIZED EFFECTIVE INGREDIENT VERSUS 1 mg TABLET WITH MICROCRYSTALLINE SOLIDS

| PARTICLE DIAMETER (µm) | | Confidence | |
|---|---|---|---|
| X50 | X100 | Interval % | RSD, % |
| 10.6 | 73 | 1.16 | 1.70 |
| Micronizate | | 1.72 | 2.56 |

A further important result is that the pharmaceutically required particle size distribution of the steroid of formula (I) can be produced with higher reproducibility and accuracy with the process according to the invention. In FIGS. 3 and 4 the development of the grain size or particle size in the crystallization process is illustrated. The scatter of the particle size distribution is clearly reduced and the maximum grain size is clearly only slightly increased in spite a multiple increase in the average particle size. This assists in attaining good CUT values, also for low-dosage formulations.

Furthermore the grain size distribution produced in the suspension also is maintained in the dried solid body.

TABLE VIII

PARTICLE SIZE DISTRIBUTION BEFORE AND AFTER DRYING

| | X10 | X50 | X90 | X100 |
|---|---|---|---|---|
| Suspension* | 2.62*** | 10.4 | 24 | 73 |
| After drying on filter | 2.7 | 10.61 | 24 | 73 |

TABLE VIII-continued

PARTICLE SIZE DISTRIBUTION BEFORE AND AFTER DRYING

| | X10 | X50 | X90 | X100 |
|---|---|---|---|---|
| Suspension** | 2.11 | 8.6 | 19 | 51 |
| After spray-drying | 2.25 | 8.03 | 17 | 43 |

*suspension of J956 in ethyl acetate with 14% by weight microcrystalline J956
**suspension of J956 in ethanol/water (90/10) with 10% by weight microcrystalline J956
***particle diameters in µm Finally a pharmaceutical formulation has been found, which provides a chemically stable and pharmaceutically effective medicinal preparation using the microcrystals produced by the process according to the invention.

Drugs with the microcrystals according to the invention made of the steroid of formula (I) can advantageously be used for the following applications. Steroids of formula (I), especially J956, are antigestagen-acting substances, which have a considerably reduced antiglucocorticoid activity in comparison to RU 486 (mifeprison), but with the same activity as RU 486 at the progesterone receptor. J956 is designated "mesoprogestin", whereby it is characterized as a compound, which has both agonistic and also antagonistic activity in vivo at the progesterone receptor (PR). Accordingly functional states can be attained that have gestagen and antigestagen activity. J956 itself is suitable for the following applications: It can be employed together with an estrogen to make a female contraceptive preparation. It can also be used for treatment and prevention of benign hormone-dependent gynecological maladies, for example for treatment of gynecological conditions, such as endometriosis, uterine fibroids, post-operative peritoneal adhesion, dysfunctional bleeding (metrorrhagia, menorrhagia) and dysmenorrhea. The daily dosage of mesoprogestin can be 0.5 mg to 100 mg, preferably 5.0 mg to 50 mg, and at its strongest amounts to 10 mg to 25 mg. J956 can similarly be used together with an estrogen as a pharmaceutical ingredient for making a medicine or ethical drug for hormone replacement therapy (HRT) and treatment of hormone deficiencies and symptoms of hormone irregularities.

The following measurement procedures are used to obtain the experimental data.

X-Ray Powder Diffractometer (X-Ray Powder Diffraction; XRPD):
Data were collected with a STOE Powder Diffractometer STADIP with a Germanium monochrometer CuK$\alpha_1$-radiation ($\lambda$=1.540598 Å)—between 30°≦2 Θ≦350°.

IR Spectroscopy:
A NICOLET 20 SXB with photoacoustic detector MTEC (KBr, 8t, 90 seconds) was used.

Particle Size Distribution:
Sympatec HELOS (H0445), dry dispersion system (RODOS), pressure 2 bar HPLC:
The purity determination took place by the following methods:
Column: Hypersil ODS, 250×4 mm; 5 µm
Eluent: acetonitrile-tetrahydrofuran mixture (3:1)/water=⅘
Flow: 1 ml/min
Detection UV (299)
Evaluation: 100% surface normalization Headspace for Residual Solvent:
 GC-autosystem with HS40 Pewrkin Elmer, column: DB-wax, 30 m×0.23 mm, FID
 Water Determination occurred according to Karl Fischer Content Uniformity Test:
 Content Determination according to USP/Ph. Eur. for individual capsules after elution through HPLC with external calibration
 Column: LiChrosphere 5µ RP-18 encapped, 150×3 mm
 Eluent: acetonitrile/water=45/55
 Flow: 1 ml/min
 Detection UV (272 nm)

Active Ingredient Release:
 Active ingredient release measured in 1000 mL water with 0.3% sodium dodecyl sulfate, 100 rpm
 Content Determination by HPLC with external calibration
 Column: LiChrosphere 5µ RP-18 encapped, 150×3 mm
 Eluent: acetonitrile/water=45/55
 Flow: 1 ml/min
 Detection UV (272 nm)

The following examples serve to illustrate the invention, but do not limit the broad concept of the invention expressed generally above or in the claims appended below.

EXAMPLES

Example 1

In a glass reactor with an anchor agitator and a double-wall heating/cooling jacket 250 g of J956 are dissolved in 1100 ml ethyl acetate at 70° C. The clear solution is cooled for 30 minutes at 35° C. A rotor-stator dispersing apparatus (Ultra Turrax, T25 basic, with S25N-25F) is used to prepare this solution. It is operated with a rotation speed of 12000 to 18000 rpm. After 2 to 5 minutes crystallization begins. The Ultra Turrax is operated for an additional 10 minutes and then is shut off.

The starting suspension obtained is heated at 55° C. and subsequently cooled within an interval of 1 hour 20 minutes to 20° C. This procedure is repeated still twice more. Subsequently the suspension is filtered by a fritte and washed with 500 ml of cold MtBE.

Subsequently the filter cake is dried with air.

Microcrystals are obtained with the following particle size distribution:

|  | Particle size (µm) |
| --- | --- |
| X10 | 2.62 |
| X50 | 10.4 |
| X90 | 23 |
| X100 | 73 |

Residual solution: 0.016% MtBE, 0.24% ethyl acetate

Example 2

In a sulfonation flask with a blade mixer and a heating/cooling bath 50 g of J956 are dissolved in 200 g of ethyl acetate at 70° C. The clear solution is cooled for 15 minutes at 35° C. A rotor-stator dispersing apparatus (Ultra Turrax, T25 basic, with S25N-25F) is operated with a rotation speed of 12000 to 16000 rpm to prepare the solution. After 2 minutes crystallization begins. The Ultra Turrax is operated for an additional 10 minutes and then is shut off.

The starting suspension obtained is heated at 50° C. and subsequently cooled within an interval of 1 hour at 20° C. This procedure is repeated still twice more.

Subsequently the suspension is filtered by means of a frit and washed with 100 ml MtBE. The filter cake is washed with 1000 ml water very thoroughly and subsequently suspended with 300 g water. The suspension is spray-dried under the following conditions in a laboratory spray-drier with two nozzles (2 mm) (QVF/Yamato):

| Drying gas entrance temperature: | 170° C. |
| --- | --- |
| Drying gas exit temperature: | 60° C. |
| Drying gas throughput: | 23 m³/min |
| Spray nozzle (d = 2 mm) | 2.5 bar |
| Feed: | 8 to 10 ml/min |

Microcrystals are obtained in a separating filter of the spray-drier with the following particle size distribution:

|  | Particle size (µm) |
| --- | --- |
| X10 | 1.75 |
| X50 | 6.04 |
| X90 | 13 |
| X100 | 36 |

0.13% water; 0.12% ethyl acetate

Example 3

A composition containing 1 mg of microcrystalline Carbamate J956 for a capsule formulation is as follow:

| SUBSTANCE | AMOUNT |
| --- | --- |
| J956, microcrystalline | 1.000 mg |
| Microcrystalline cellulose | 102.480 mg |
| Magnesium stearate | 0.520 mg |
| Hard gelatin capsule, size 3 | 1 piece |
| Capsule filling mass | 104.000 mg |

Microcrystalline J956 is mixed with microcrystalline cellulose in a suitable mixer (e.g. container mixer). The magnesium stearate is added and mixed several times. The absence of water in the unit is tested. The mixture is filled in a hard gelatin capsule, size 3, with a suitable capsule filling machine (e.g. Harro Hoeflinger, KFMIIIC).

Example 4

A composition containing 1 mg of microcrystalline Carbamate J956 for a tablet is as follow:

| CORE: | |
| --- | --- |
| J956, microcrystalline | 1.00 mg |
| Lactose monohydrate | 33.8 mg |
| Corn starch | 18.0 mg |
| Maltodextrin (10% water) | 6.0 mg |

| -continued | |
|---|---|
| Na carboxymethyl starch | 0.6 mg |
| Glycerol monobehenate | 0.6 mg |
| SHELL: | |
| Hydroxypropylmethyl cellulose | 1.125 mg |
| Talcum | 0.225 mg |
| Titanium dioxide | 0.625 mg |
| Iron oxide, yellow pigment | 0.020 mg |
| Iron oxide, red pigment | 0.005 mg |

The microcrystalline J956 is mixed with lactose and corn starch in a granulator (e.g. a fluidized bed granulator GPCG 3.1, Glatt Co.). A solution of malto-dextrin in water is sprayed into the mixture. The arising granulate is then dried (input air temperature 70° C.). The granulate is mixed with Na- carboxy-methyl starch and glycerol monobehenate and 150 mg of the resulting mass is pressed to form the tablet core. The tablet core is then sprayed with a suspension of the coating substance in water by means of a suitable coater (e.g. Driacoater 500, Driam). The film arising on the tablet core is then dried (film mass 4 mg, input air temperature 70° C., drying loss of the film tablet 3%).

The disclosure in German Patent Application 102 18 109.8 of Apr. 23, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a process for production of crystals of 11β-benzaldoxim-estra-4,9-diene derivatives, crystals obtained thereby and pharmaceutical preparations containing them, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A process for making crystals of a 11β-benzaldoxim-estra-4,9-diene derivative, said crystals having an average particle size of from 3 μm to 25 μm and a maximum particle size of 100 μm, said process comprising subjecting a super-saturated solution containing said 11β-benzaldoxim-estra-4,9-diene derivative to a wet milling by a wet milling apparatus while crystallizing, in order to obtain a primary particle suspension;

wherein said 11β-benzaldoxim-estra-4,9-diene derivative is a compound of formula (I), or a pharmacologically acceptable salt thereof:

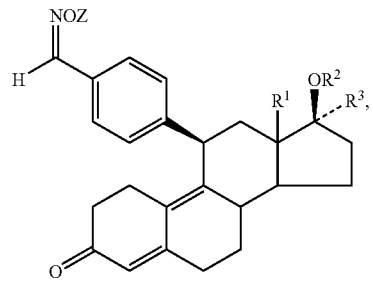

wherein $R^1$ represents hydrogen or an alkyl group with 1 to 6 carbon atoms;

$R^2$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or a —CONHR$^4$ group, $R^3$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, or a —(CH$_2$)$_n$—CH$_2$X, an —OR$^5$ group, a —(CH$_2$)$_o$—CH=CH(CH$_2$)$_p$—R$^6$ group or —(CH$_2$)$_q$C=CR$^7$;

wherein n is 0, 1 or 2, o is 0, 1, 2 or 3, p is 0, 1 or 2 and q is 0, 1 or 2;

wherein X represents hydrogen, a fluoro group, a chloro group, a bromo group, an iodo group, a cyano group, an azido group, a rhodano group, an —OR$^5$ group or an —SR$^5$ group;

wherein Z represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms, a —CONHR$^4$ group, a —COOR$^4$ group, an alkali metal atom or an alkaline earth metal atom;

wherein $R^4$ represents an alkyl group with 1 to 10 carbon atoms, an aryl group with 1 to 10 carbon atoms, an aralkyl group with 1 to 10 carbon atoms or an alkylaryl group with 1 to 10 carbon atoms;

wherein $R^5$ represents hydrogen, an alkyl group with 1 to 10 carbon atoms, an awl group with 1 to 10 carbon atoms, an aralkyl group with 1 to 10 carbon atoms, an alkylaryl group with 1 to 10 carbon atoms or an acyl group with 1 to 10 carbon atoms;

wherein $R^6$ represents a hydrogen, a hydroxy group, an alkyl group with 1 to 10 carbon atoms, an alkoxy group with 1 to 10 carbon atoms, an awl group with 1 to 10 carbon atoms, an aralkyl group with 1 to 10 carbon atoms, an alkylaryl group with 1 to 10 carbon atoms, an acyl group with 1 to 10 carbon atoms or an acyloxy group with 1 to 10 carbon atoms; and wherein $R^7$ represents a hydrogen, a fluoro group, a chloro group, a bromo group, an iodo group, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms.

2. The process as defined in claim 1, wherein said 11β-benzaldoxim-estra-4,9-diene derivative is 11β-{4-[(ethylaminocarbonyl)oximinomethyl]phenyl}-7β-methoxy-17α-methoxymethyl-estra-4,9-dien-3-one.

3. The process as defined in claim 1, wherein said supersaturated solution contains from 10 to 30 percent by weight of said compound of said formula (I), based on said supersaturated solution.

4. The process as defined in claim 3, wherein said supersaturated solution comprises a solvent and said solvent is ethyl acetate.

5. The process as defined in claim 1, further comprising preparing said supersaturated solution by dissolving said compound of formula (I) in a solvent at a temperature below a boiling point of said solvent to form a resulting solution and subsequently cooling said resulting solution to a temperature above a freezing point of the resulting solution.

6. The process as defined in claim 1, wherein said crystallizing is performed in a vessel or container having a stirring device.

7. The process as defined in claim 1, wherein said wet milling apparatus is a rotor-stator apparatus, a stirring mill, a roller mill or a colloid mill.

8. The process as defined in claim 1, further comprising heating said primary particle suspension to a temperature ($T_{max}$) below a solubility limit of primary particles of the primary particle suspension and subsequently cooling to a temperature above a freezing point ($T_{min}$) of the primary particle suspension.

9. The process as defined in claim 8, wherein said supersaturated solution comprises a solvent and said temperature ($T_{max}$) below said solubility limit is selected so that from 10 to 90 percent by weight of said primary particles dissolve in said solvent.

10. The process as defined in claim 8, wherein said temperature above said freezing point ($T_{min}$) is selected so that dissolved primary particles are substantially re-crystallized.

11. The process as defined in claim 8, wherein said cooling from said temperature ($T_{max}$) below said solubility limit to said temperature above said freezing point ($T_{min}$) occurs during a time interval of 1 minute to 10 hours.

12. The process as defined in claim 8, wherein said heating to said temperature ($T_{max}$) below said solubility limit and said cooling to said temperature above said freezing point is performed from 1 to 10 times.

13. Crystals of a 11β-benzaldoxim-estra-4,9-diene derivative having an average particle size at from 3 μm to 25 μm and a maximum particle size of 100 μm, wherein said crystals are made by a process comprising subjecting a supersaturated solution containing said 11β-benzald-oxim-estra-4,9-diene derivative to a wet milling by a wet milling apparatus while crystallizing, in order to obtain a primary particle suspension;

wherein said 11β-benzaldoxim-estra-4.9-diene derivative is a compound of formula (I), or a pharmacologically acceptable salt thereof:

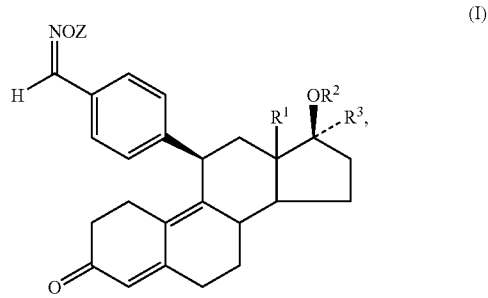

wherein $R^1$ represents hydrogen or an alkyl group with 1 to 6 carbon atoms;

$R^2$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or a —$CONHR^4$ group, $R^3$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms or a —$(CH_2)_n$—$CH_2X$, an —$OR^5$ group, a —$(CH_2)_o$—CH=CH$(CH_2)_p$—$R^6$ group or —$(CH_2)_q$C=$CR^7$;

wherein n is 0, 1 or 2, o is 0, 1, 2 or 3, p is 0, 1 or 2 and q is 0, 1 or 2;

wherein X represents hydrogen, a fluoro group, a chloro group, a bromo group, an iodo group, a cyano group, an azido group, a rhodano group, an —$OR^5$ group or an —$SR^5$ group;

wherein Z represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms, a —$CONHR^4$ group, a —$COOR^4$ group, an alkali metal atom or an alkaline earth metal atom;

wherein $R^4$ represents an alkyl group with 1 to 10 carbon atoms, an aryl group with 1 to 10 carbon atoms, an aralkyl group with 1 to 10 carbon atoms or an alkylaryl group with 1 to 10 carbon atoms;

wherein $R^5$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms;

wherein $R^6$ represents a hydrogen, a hydroxy group, an alkyl group with 1 to 10 carbon atoms, an alkoxy group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or an acyloxy group with 1 to 10 carbon atoms; and wherein $R^7$ represents a hydrogen, a fluoro group, a chloro group, a bromo group, an iodo group, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms.

14. The crystals as defined in claim 13, wherein said 11β-benzaldoxim-estra-4,9-diene derivative is 11β-{4-[(ethylaminocarbonyl)oximinomethyl]phenyl}-17β-methoxy-17α-methoxymethyl-estra-4,9-dien-3-one.

15. The crystals as defined in claim 13, wherein said supersaturated solution contains from 10 to 30 percent by weight of said 11β-benzaldoxim-estra-4.9-diene derivative, based on said supersaturated solution, and said process comprises preparing said supersaturated solution by dissolving said 11β-benzaldoxim-estra4,9-diene derivative in a solvent at a temperature below a boiling point of said solvent to form a resulting solution and subsequently cooling said resulting solution to a temperature above a freezing point of the resulting solution.

16. The crystals as defined in claim 15, wherein said supersaturated solution comprises a solvent and said solvent is ethyl acetate.

17. The crystals as defined in claim 13, wherein said supersaturated solution comprises a solvent; said process comprises heating said primary particle suspension to a temperature ($T_{max}$) below a solubility limit of primary particles of the primary particle suspension and subsequently cooling to a temperature above a freezing point ($T_{min}$) of the primary particle suspension and wherein said temperature ($T_{max}$) below said solubility limit is selected so that from 10 to 90 percent by weight of said primary particles dissolve in said solvent and said temperature above said freezing point ($T_{min}$) is selected so that dissolved primary particles are substantially re-crystallized, said cooling from said temperature ($T_{max}$) below said solubility limit to said temperature above said freezing point ($T_{min}$) occurs during a time interval of 1 minute to 10 hours.

18. The crystals as defined in claim 13, wherein said crystallizing is performed in a vessel or container having a stirring device and said wet milling apparatus is a rotor-stator apparatus, a stirring mill, a roller mill or a colloid mill.

19. A pharmaceutical preparation containing crystals of 11β-benzaldoxim-estra-4,9-diene derivative, said crystals having an average particle size of from 3 μm to 25 μm and a maximum particle size of 100 μm, wherein said crystals are made by a process comprising subjecting a supersaturated solution containing the 11β-benzaldoxim-estra-4,9-diene derivative to a wet milling by a wet milling apparatus while crystallizing, in order to obtain a primary particle suspension;

wherein said 11β-benzaldoxim-estra-4,9-diene derivative is a compound of formula (I), or a pharmacologically acceptable salt thereof:

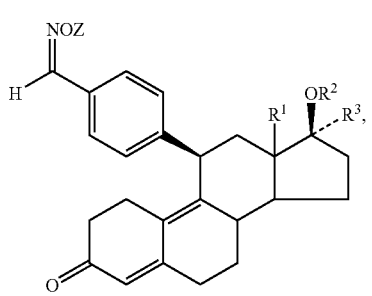

(I)

wherein $R^1$ represents hydrogen or an alkyl group with 1 to 6 carbon atoms;

$R^2$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or a —CONHR$^4$ group, $R^3$ represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, or a —(CH$_2$)$_n$—CH$_2$X, an —OR$^5$ group, a —(CH$_2$)$_o$—CH=CH(CH$_2$)$_p$R$^5$ group or —(CH$_2$)$_q$C=CR$^7$;

wherein n is 0, 1 or 2, o is 0, 1, 2 or 3, p is 0, 1 or 2 and q is 0, 1 or 2;

wherein X represents hydrogen, a fluoro group, a chloro group, a bromo group, an iodo group, a cyano group, an azido group, a rhodano group, an —OR$^5$ group or an —SR$^5$ group;

wherein Z represents hydrogen, an alkyl group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms, a —CONHR$^4$ group, a —COOR$^4$ group, an alkali metal atom or an alkaline earth metal atom;

wherein R$^4$ represents an alkyl group with 1 to 10 carbon atoms, an aryl group with 1 to 10 carbon atoms, an aralkyl group with 1 to 10 carbon atoms or an alkylaryl group with 1 to 10 carbon atoms;

wherein R$^5$ represents hydrogen, an alkyl group with 1 to 10 carbon atoms, an aryl group with 1 to 10 carbon atoms, an aralkyl group with 1 to 10 carbon atoms, art alkylaryl group with 1 to 10 carbon atoms or an acyl group with 1 to 10 carbon atoms;

wherein R$^6$ represents a hydrogen, a hydroxy group, an alkyl group with 1 to 10 carbon atoms, an alkoxy group with 1 to 10 carbon atoms, an aryl group with 1 to 10 carbon atoms, an aralkyl group with 1 to 10 carbon atoms, an alkylaryl group with 1 to 10 carbon atoms, an acyl group with 1 to 10 carbon atoms or an acyloxy group with 1 to 10 carbon atoms; and wherein R$^7$ represents a hydrogen, a fluoro group, a chloro group, a bromo group, an iodo group, an alkyl group with 1 to 10 carbon atoms, an aryl group with 1 to 10 carbon atoms, an aralkyl group with 1 to 10 carbon atoms, an alkylaryl group with 1 to 10 carbon atoms or an acyl group with 1 to 10 carbon atoms.

20. The pharmaceutical preparation as defined in claim 19, wherein said 11β-benzaldoxim-estra-4,9-diene derivative is 11β-{4[(ethylaminocarbonyl)-oximino-methyl]-phenyl}-17β-methoxy-17α-methoxymethyl-estra-4,9-dien-3-one.

21. The pharmaceutical preparation as defined in claim 19, wherein said crystallizing is performed in a vessel or container having a stirring device and said wet milling apparatus is a rotor-stator apparatus, a stirring mill, a roller mill or a colloid mill.

22. The pharmaceutical preparation as defined in claim 19, wherein said supersaturated solution contains from 10 to 30 percent by weight of said 11β-benzaldoxim-estra-4,9-diene derivative, based on said supersaturated solution, and said process comprises preparing said supersaturated solution by dissolving said 11β-benzaldoxim-estra-4,9-diene derivative in a solvent at a temperature below a boiling point of said solvent to form a resulting solution and subsequently cooling said resulting solution to a temperature above a freezing point of the resulting solution.

23. The pharmaceutical preparation as defined in claim 22, wherein said solvent is ethyl acetate.

* * * * *